United States Patent
Patella et al.

(10) Patent No.: US 10,058,241 B2
(45) Date of Patent: Aug. 28, 2018

(54) SYSTEMS AND METHODS FOR IMPROVED VISUAL FIELD TESTING

(71) Applicant: Carl Zeiss Meditec, Inc., Dublin, CA (US)

(72) Inventors: Vincent Michael Patella, Albany, CA (US); Jeffrey Donald Stevens, Pleasanton, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 0 days.

(21) Appl. No.: 15/439,369

(22) Filed: Feb. 22, 2017

(65) Prior Publication Data
US 2017/0245752 A1    Aug. 31, 2017

Related U.S. Application Data

(60) Provisional application No. 62/301,229, filed on Feb. 29, 2016.

(51) Int. Cl.
| | | |
|---|---|---|
| *A61B 3/02* | (2006.01) | |
| *A61B 3/00* | (2006.01) | |
| *A61B 3/024* | (2006.01) | |

(52) U.S. Cl.
CPC ............ *A61B 3/024* (2013.01); *A61B 3/0025* (2013.01); *A61B 3/0041* (2013.01); *A61B 3/0075* (2013.01); *A61B 3/0083* (2013.01)

(58) Field of Classification Search
CPC ....... A61B 3/024; A61B 3/0091; A61B 3/032; A61B 3/0033; A61B 3/0041
USPC .................................................. 351/200–246
See application file for complete search history.

(56) References Cited

U.S. PATENT DOCUMENTS

| | | |
|---|---|---|
| 3,718,386 A | 2/1973 | Lynn et al. |
| 5,220,361 A | 6/1993 | Lehmer et al. |
| 5,381,195 A | 1/1995 | Rootzen et al. |
| 5,491,757 A | 2/1996 | Lehmer et al. |
| 5,598,235 A | 1/1997 | Heijl et al. |
| 7,401,921 B2 | 7/2008 | Baker et al. |
| 8,132,916 B2 | 3/2012 | Johansson |
| 8,668,338 B2 | 3/2014 | Johansson et al. |
| 8,684,529 B2 | 4/2014 | Johansson et al. |
| 9,179,833 B2 | 11/2015 | Narasimha-Iyer et al. |
| 2011/0299034 A1* | 12/2011 | Walsh ............... A61B 3/102 351/206 |

(Continued)

*Primary Examiner* — Mohammad Hasan
(74) *Attorney, Agent, or Firm* — Morrison & Foerster LLP

(57) ABSTRACT

Systems and methods for performing a visual field test of a patient are described. One example method for performing the visual field test of the patient using a visual field testing device having a refractive correction element, a patient support, and a motor operably attached to one of the refractive correction element or the patient support includes positioning the patient's head relative to the device using the patient support. An image showing the position of the eye relative to the refractive correction element is collected. The relative displacement of the eye with respect to the refractive correction element is determined based on the collected image. The motor is actuated in a manner to reduce the determined displacement. A series of test stimuli is displayed to the patient's eye and responses to the test stimuli are received from the patient. The responses are analyzed to make an assessment of the patient's visual field.

17 Claims, 6 Drawing Sheets

(56) References Cited

U.S. PATENT DOCUMENTS

2012/0287401 A1* 11/2012 Bizios .................. A61B 3/0025
351/206
2013/0044290 A1* 2/2013 Kawamura ............ A61B 3/032
351/201
2013/0070204 A1* 3/2013 Johansson .............. A61B 3/024
351/224

* cited by examiner

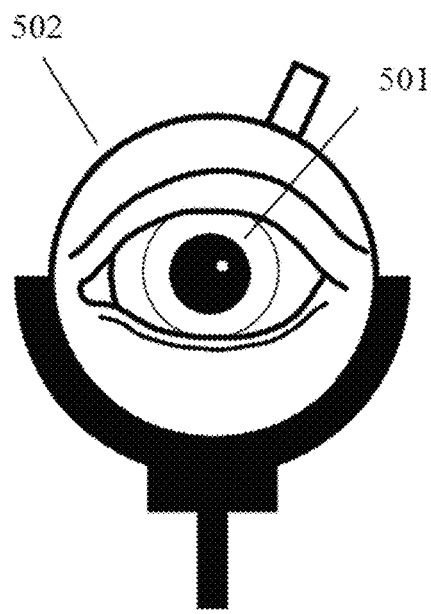
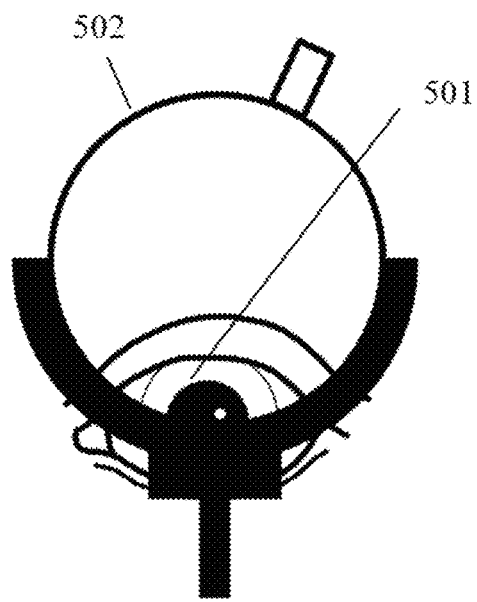
FIG. 5(a)          FIG. 5(b)
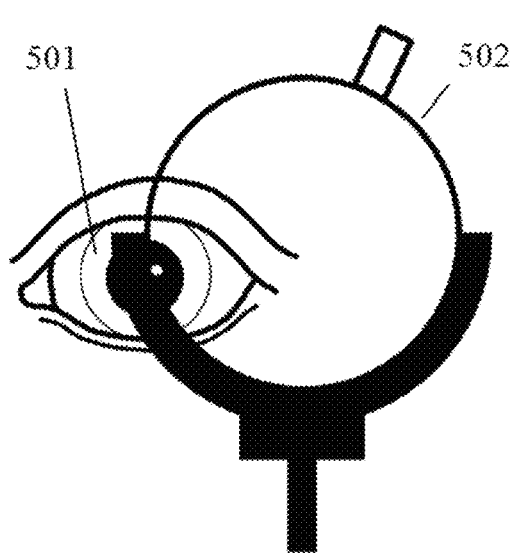
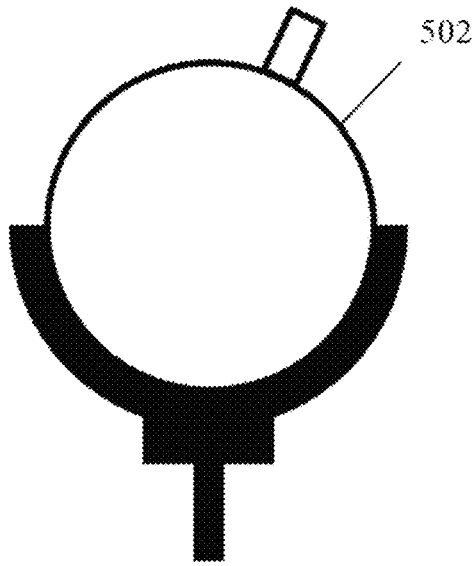
FIG. 5(c)          FIG. 5(d)

SYSTEMS AND METHODS FOR IMPROVED VISUAL FIELD TESTING

PRIORITY

This application claims priority to U.S. Provisional Application Ser. No. 62/301,229, filed Feb. 29, 2016, the contents of which are hereby incorporated by reference.

TECHNICAL FIELD OF THE INVENTION

The present application relates to the field of aligning a patient's eye relative to a refractive correction element. In particular, it discloses an approach for automatically positioning the patient's eye relative to the center of the refractive correction element. This is particularly useful for visual field testing devices that use liquid trial lenses or conventional ophthalmic trial lenses or other means of refraction correction.

BACKGROUND

A lens is often used for refractive correction during a course of perimetry or other types of visual field testing of a patient. One example of refractive correction is a liquid trial lens (see for example U.S. Pat. No. 8,668,338, the contents of which are hereby incorporated by reference), which may be more sensitive to patient eye alignment than other trial lenses. Prior to beginning a perimetry test, a technician operating the perimeter typically tries to center a patient's eye at or near the z-axis (the axis of symmetry) of the perimeter's bowl. Live image(s) or video of the eye, captured using the instrument's camera, are displayed to the technician for patient alignment or test verification purposes. The technician sets an initial patient pupil position by adjusting the chin rest until the eye is determined to be centered in the displayed eye video. This initial position may or may not be centered on the refractive correction lens in use. Further, patients move around during the course of the testing. Due to these factors, the patient's eye is often misaligned with the correction lens, or becomes misaligned during the course of testing. This misalignment can result in 1) poor gaze monitor performance, 2) trial lens rim artifacts in the visual field report, and 3) degraded retinal sensitivity measurements due to stimulus blur induced by such decentration of the eye relative to the lens center.

Some perimeters use a set of fixed focus trial lenses for refraction correction. These lenses typically may not be as sensitive to decentration as is a liquid trial lens with regard to successful gaze monitor performance, but still can generate trial lens artifacts if the eye is not accurately aligned to the center of the lens. Thus, there is a need for an approach that can correctly position or align a patient's eye to the center of the refractive correction lens.

SUMMARY

According to one aspect of the subject matter described in the present application, a method for performing a visual field test of a patient using a visual field testing device having a refractive correction element, a patient support, and a motor operably attached to one of the refractive correction element or the patient support for changing the location of the refractive correction element relative to the patient support includes positioning the patient's head relative to the visual field testing device using the patient support; collecting an image of the patient's eye, said image displaying the position of the eye relative to the refractive correction element; determining the relative displacement of the patient's eye with respect to the refractive correction element based on the collected image; actuating the motor in a manner to reduce the determined displacement; displaying a series of test stimuli to the eye of the patient; receiving responses to the test stimuli from the patient; analyzing the received responses to make an assessment of the patient's visual field; and displaying or storing the assessment or a further analysis thereof.

According to another aspect of the subject matter described in the present application, a visual field system for performing a visual field test of a patient includes a patient support for positioning the patient's head relative to the system; a refractive correction element operably attached to said system for correcting the refractive error of the patient; a motor operably attached to one of the refractive correction element or the patient support for changing the location of the refractive correction element with respect to the patient support; a camera for capturing an image of the patient's eye, said image displaying the position of the patient's eye relative to the refractive correction element; a processor for determining the relative displacement of the patient's eye with respect to the refractive correction element based on the captured image and actuating the motor in a manner to reduce the determined displacement; a display for displaying a series of test stimuli to the eye of the patient; and a response mechanism for receiving patient responses to the test stimuli.

The visual testing system of the present application automatically aligns the patient eye to the center of the refractive correction element (e.g., liquid trial lens) rather than using an initial position established by the attending technician. It does so by 1) finding the perimeter of the element (e.g., clear lens aperture), 2) calculating the location of the center of the element, and 3) locating the center of the eye's pupil. In a preferred embodiment, the system drives the x- and y-axis chin rest motors, moving the patient to minimize the separation distance between the refractive correction element's center and the patient's pupil center. The separation distance is measured in the plane of images provided by the system's camera. In this way, the system centers the eye relative to the refractive correction element and compensates for small patient head movements.

The automatic alignment of the refractive correction element with the patient's eye discussed herein is advantageous in a number of respects. For instance, the system continually (i.e. frequently, and during the entire course of a perimetry test) re-centers the patient's eye relative to the refractive correction element. A properly centered eye can minimize 1) magnitude of errors in patient gaze estimation, 2) lens rim artifacts, and 3) likelihood of retinal sensitivity errors due to stimulus blur.

The features and/or advantages described herein are not all-inclusive and many additional features and/or advantages will be apparent to one of ordinary skill in the art in view of the figures and description. Moreover, it should be noted that the language used in the specification has been principally selected for readability and instructional purposes and not to limit the scope of the inventive subject matter.

BRIEF DESCRIPTION OF THE DRAWINGS

FIG. 2(a) shows a liquid trial lens encapsulating a volume of liquid with a specific refractive index. FIGS. 2(b) and 2(c) shows exemplary convex and concave lenses, respectively, when the distribution of the volume of liquid in the lens of FIG. 2(a) is changed.

FIGS. 5(a)-5(d) illustrate example images depicting positioning of an eye relative to a lens. In particular, FIG. 5(a) shows a case of optimum positioning, FIG. 5(b) shows a case of vertical displacement, FIG. 5(c) shows a case of horizontal displacement, and FIG. 5(d) shows a case of total absence of the eye.

DETAILED DESCRIPTION

All patent and non-patent references cited within this specification are herein incorporated by reference in their entirety to the same extent as if the disclosure of each individual patent and non-patient reference was specifically and individually indicated to be incorporated by reference in its entirely.

Figure 1:
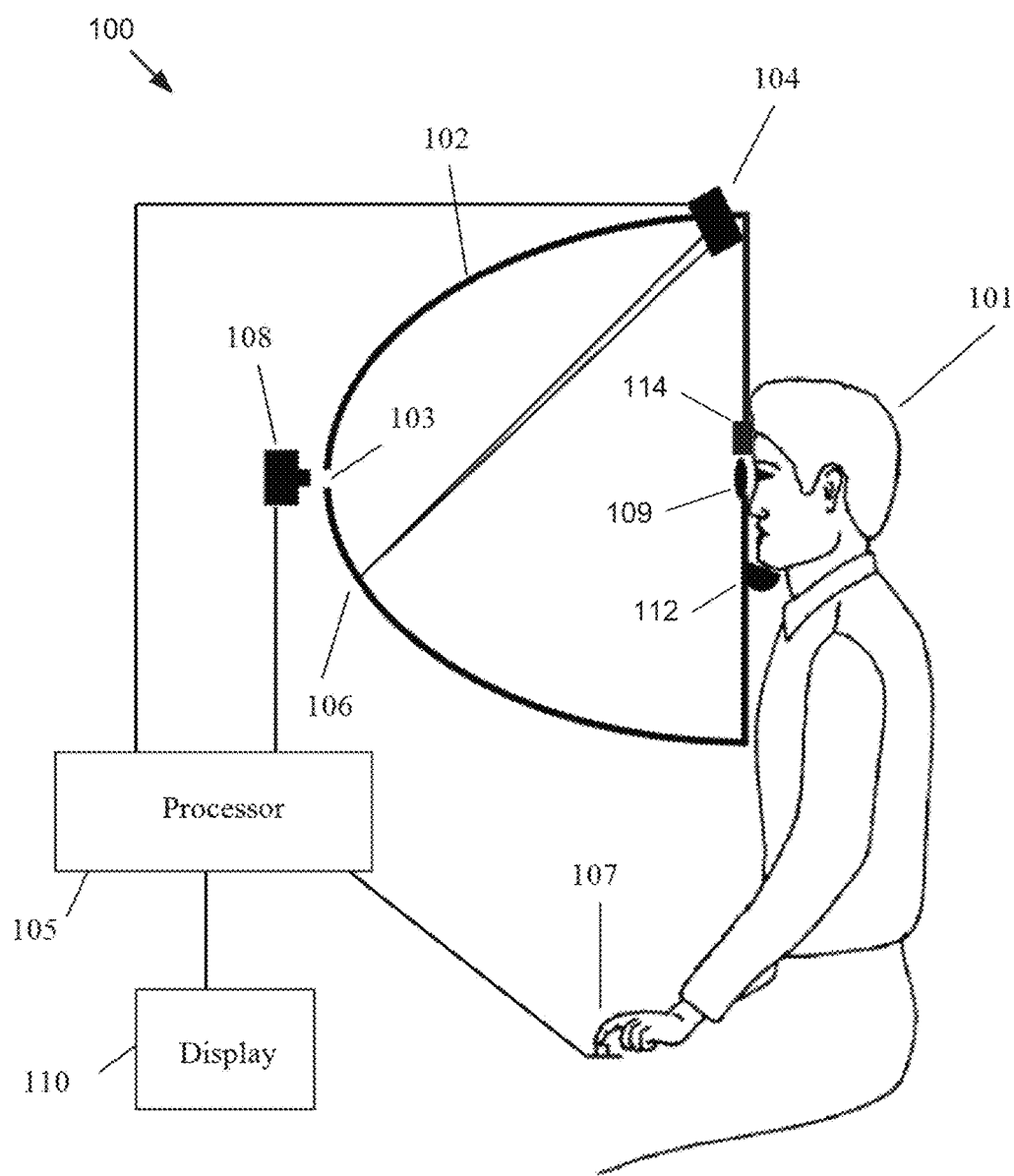
FIG. 1 illustrates one example of a visual field test system that can be used to practice the present invention.

The automated alignment approach described herein could be used in conjunction with any type of visual field tester or perimeter containing a refractive correction element 109, such as a liquid trial lens. One such system 100 is illustrated in FIG. 1. A subject 101 is shown observing a hemispherical projection screen 102. The subject is instructed to fixate at a point at the center of the hemispherical screen 103. The subject's head contacts a patient support, in this case, the subject rests his/her head on the chin rest 112 and places his/her forehead against the forehead rest 114. A motor (not shown) may be operably attached to the patient support that when actuated moves the chin rest 112 and/or the forehead rest 114 to correctly position the patient's eye relative to the refractive correction element 109. The chin rest 112 and the forehead rest 114 can be moved together or independently of one another. In one embodiment, the chin rest and headrest move independently in the vertical direction to accommodate different patient head sizes and move together in the horizontal direction. However, this is not limiting and other arrangements/movements can be envisioned by one skilled in the art. A projector 104 under control of a processor 105 projects a series of test stimuli 106 onto the screen. The subject 101 indicates that a stimulus 106 was seen by depressing button 107. The response is recorded by processor 105, which can analyze the response to make an assessment of the patient's visual field. A camera 108 can be used to capture the gaze of the patient and the position of the eye relative to the refractive correction element throughout the test. In a preferred embodiment, as depicted in FIG. 1, the camera 108 is located at the z-axis and behind the bowl for capturing live images(s) or video of the patient's eye. In other embodiments, this camera may be located off the z-axis, in which case it may be necessary to account for displacement from the z-axis in order to calculate proper alignment of the eye with the refractive correction element. The images from the gaze camera 108 can optionally be displayed on display 110 to the clinician (also interchangeably referred to herein as a technician) for aid in patient alignment or test verification. A refractive correction element 109 is connected to the system and positioned in front of the eye of the subject being tested to correct the refractive error of the subject. The element 109 may be placed approximately 13 mm from the patient's eye. In some instances, a motor (not shown) may be connected to the refractive correction element 109 that when actuated by the processor 105 causes the element 109 to move in a direction to appropriately align the center of the refractive correction element 109 with the center of the patient's pupil as discussed later below. In some embodiments, one or more light sources (not shown) may be positioned in front of the eye of the subject 101, which create reflections from ocular surfaces such as the cornea. In one variation, the light sources may be light-emitting diodes (LEDs). While FIG. 1 shows a projection type visual field tester, the invention described herein can be used with other types of devices, including those that generate images through LCD or other displays (see for example U.S. Pat. No. 8,132,916, hereby incorporated by reference.) The invention described herein also can be used with devices that have built-in methods/means of refractive correction (e.g., a Badal optometer), other than a liquid lens or conventional trial lens. For instance, a Badal optometer built into a visual field testing device can align a patient's eye relative to the exit pupil of the device and correct for any refractive error(s).

The camera 108 can record and store one or more images of the eye during each stimulus presentation. This may lead to the collection of anywhere from tens to hundreds of images per visual field test, depending on the testing conditions. Alternatively, the camera 108 may record and store a full length movie during the test and provide time stamps when each stimulus is presented. Additionally, images may also be collected between stimulus presentations to provide details on the subject's overall attention throughout the test's duration.

Figures 2A, 2B, 2C:
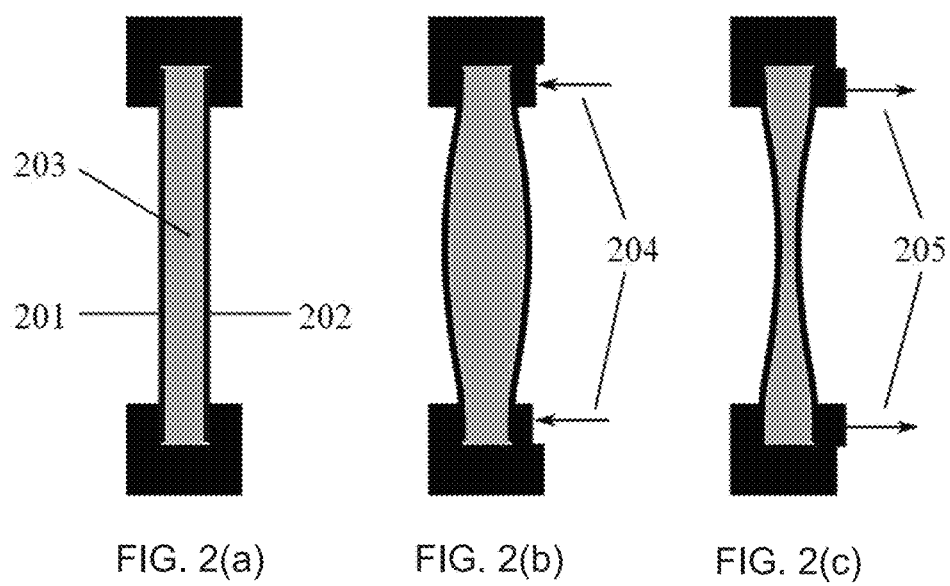
FIGS. 2(a)-2(c) illustrate a liquid trial lens that could be used as the refractive correction element in the visual field test system of FIG. 1. In particular.

In a preferred embodiment of the present invention, the refractive correction element 109 comprises a tunable optical element such as a liquid trial lens (see for example U.S. Pat. No. 8,668,338, the contents of which are hereby incorporated by reference), which is utilized to provide a variable refractive correction of the subject 101. However, it should be noted that the present invention is not limited to using the liquid trial lens for refractive correction and other types of adjustable lenses and conventional/standard trial lenses known in the art can also be used with the present invention. An example liquid trial lens is depicted in FIGS. 2(a)-2(c). A liquid trial lens typically consists of one or two transparent and flexible membranes 201 and 202, encapsulating a volume of liquid 203 with a specific refractive index, as shown in FIG. 2(a). An actuator changes the distribution of the volume of the liquid, to adjust the refractive power of the lens as shown pictorially in FIGS. 2(b) and 2(c) creating convex and concave lenses respectively. In this case, pressure is applied or released to the periphery of the lens as indicated by arrows 204 and 205. The volume change can be accomplished either manually or automatically by the instrument, by turning the radius of an annular sealing ring, or by squeezing or releasing the periphery of the lens or other method which changes the profile of the lens or volume of the liquid. A liquid trial lens for perimetry would typically have 36 mm clear aperture to ensure the patient can be tested within ±30° visual field. The range would typically be from −10 to +10 diopter, but could be, e.g., offset with lenses to target high myopic or hyperopic populations. A liquid lens can also be used to provide cylindrical correction of a patient's astigmatism.

One of the previous approaches for centering or aligning a patient's eye with a refractive correction lens involved a technician setting an initial pupil position, which may or may not be centered on the refractive correction lens as discussed elsewhere herein. Example of such a scenario is depicted via images FIGS. 5(a)-5(d). FIG. 5(a) shows an eye 501 properly positioned behind a lens 502 as would be desired. FIG. 5(b) shows when the eye 501 is low relative to the lens 502 and FIG. 5(c) shows when the eye 501 is laterally displaced from the lens 502. FIG. 5(d) shows the complete absence of the eye that would result if the patient has temporarily removed their head away from the perimeter.

An embodiment of the present invention includes an instrument control algorithm, which may be software, code, and/or a routine that uses existing hardware signals and a motorized positioning system to automatically position the patient's eye at the center of the refractive correction lens placed in front of the eye. The algorithm can be used with any type of visual field tester or perimeter (e.g., the visual field test system shown in FIG. 1). With reference to FIG. 1, a patient rests his/her head on the patient support that includes the chin rest 112 and the forehead rest 114 (see for example, U.S. Pat. No. 7,401,921). The chin rest 112 and the forehead rest 114 can be moved, for example, by stepper motors under software control. A rocker switch enables the attending technician to adjust the patient's head position by causing the chin rest and forehead motors to operate. An adjustable refractive correction element 109 is placed in front of the patient's eye as close to the patient's eye as possible without adversely affecting the patient's comfort. In some embodiments, the element is placed approximately 13 mm from the patient's eye. A camera 108, located behind the perimeter bowl on the z-axis of the bowl (the axis of symmetry), provides real time video display of the patient's eye.

Figure 3:
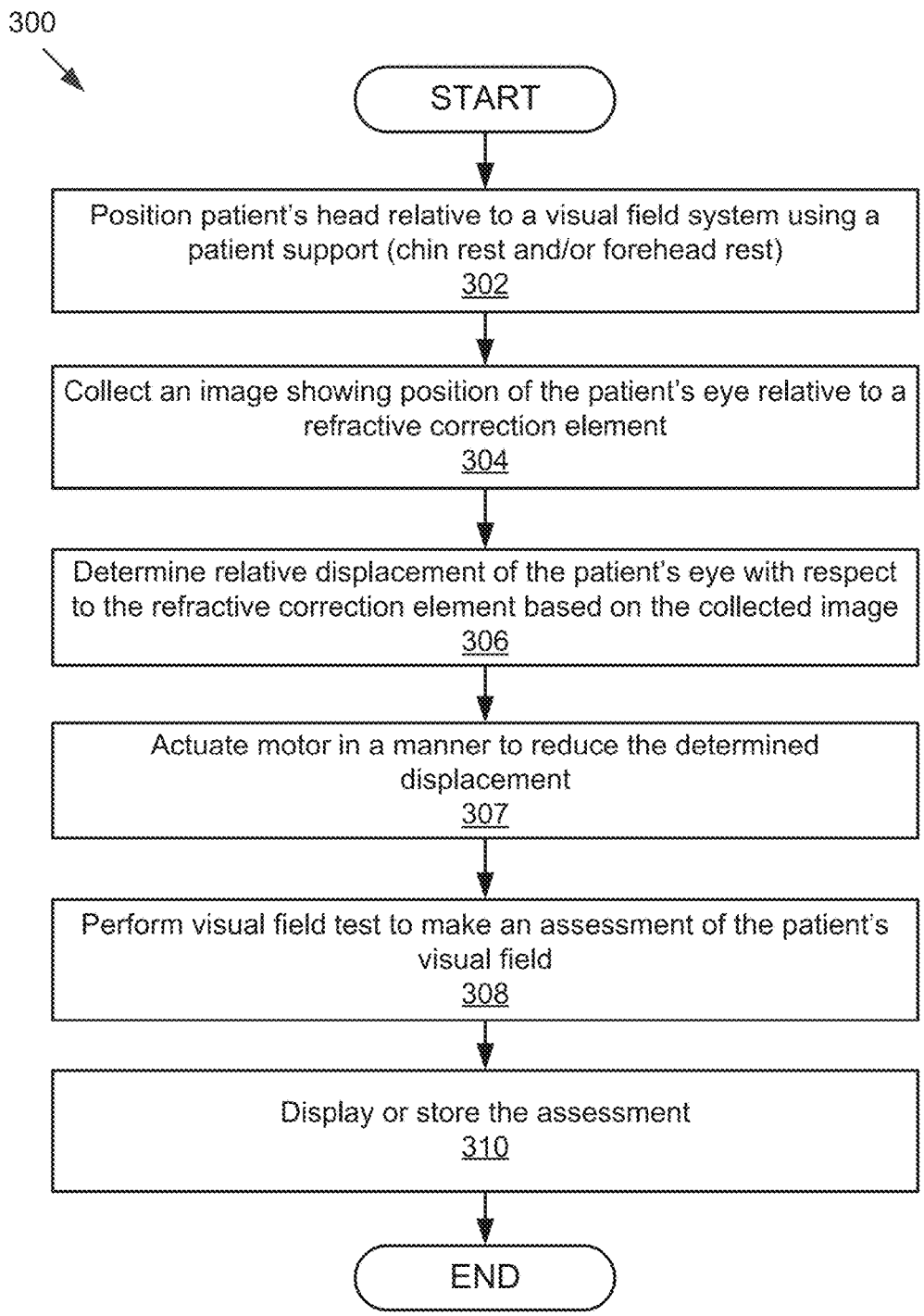
FIG. 3 is a flowchart of an example method for performing a perimetry or visual field test of a patient according to one embodiment of the present invention.

FIG. 3 is a flowchart of an example method 300 for performing a perimetry or visual field test of a patient according to one embodiment of the present invention. In step 302, the patient's head is positioned relative to a visual field system (e.g., the visual field system 100) having the refractive correction element 109 using a patient support (chin rest and/or forehead rest depending on the specific visual test system), typically by the attending technician. The technician may try to manually center the patient's eye relative to the refractive correction element by adjusting the chin rest and the forehead rest using the rocker switch. This is an initial/rough alignment done by the technician prior to the automatic and more precise alignment performed by the system itself as discussed in further detail below with respect to steps 402-412 in FIG. 4. In some instances, the visual field system may be a self-testing system and step 302 may be performed by the patient himself as discussed in further detail below.

In step 304, an image is collected showing the patient's eye and a small area it including the refractive correction lens 109 (e.g., see images displayed in FIGS. 5(a)-5(d)). The image is captured using the camera 108 as discussed in FIG. 1. In step 306, the relative displacement of the patient's eye with respect to the refractive correction element is determined using the collected image, as discussed in further detail below with respect to FIG. 4. In step 307, the motor(s) of the patient support and/or the refractive correction element are actuated in a manner to reduce the determined displacement. In one instance, the motor of the patient support causes the chin rest and/or forehead rest to move in a direction so that the center of patient's eye is properly aligned with the center of the refractive correction element and therefore the determined displacement is reduced/eliminated. In another instance, the motor of the refractive correction element causes it to move with respect to the patient support so that this displacement is reduced/eliminated. The patient support and the refractive correction element can be moved together or independently of one another to reduce the determined displacement. Steps 306 and 307 are performed as part of the instrument control algorithm 605 (see FIG. 6) and comprise the automatic alignment process of the visual field system. In some embodiments, the steps 304, 306, and 307 may be executed for each test stimulus presentation. In other embodiments, these steps may be executed once during the course of the testing (e.g., initial check before starting the very first perimetry test of the patient) or may be executed in periodic intervals (e.g., after every certain minutes or may be after every specific number of test stimuli are presented to the patient).

Once the displacement is reduced, a visual field test is initiated to make an assessment of the patient's visual field (step 308), and the results of such assessment is displayed or stored for future access and/or retrieval (step 310). As discussed in FIG. 1, the visual field test includes displaying a series of test stimuli to the patient, receiving a response from the patient to one or more stimuli, and analyzing the patient response to make an assessment of the patient's visual field.

In some implementations, the steps of FIG. 3 may be performed in a self-driven environment without involving a technician as discussed above. For instance, the visual field testing system discussed herein may be a self-testing system which a patient may operate to obtain visual field test results of his/her eye. Such a self-testing system may be located at a marketplace, patient's home, an eye clinic, and/or an ophthalmologist workplace.

Figure 4:
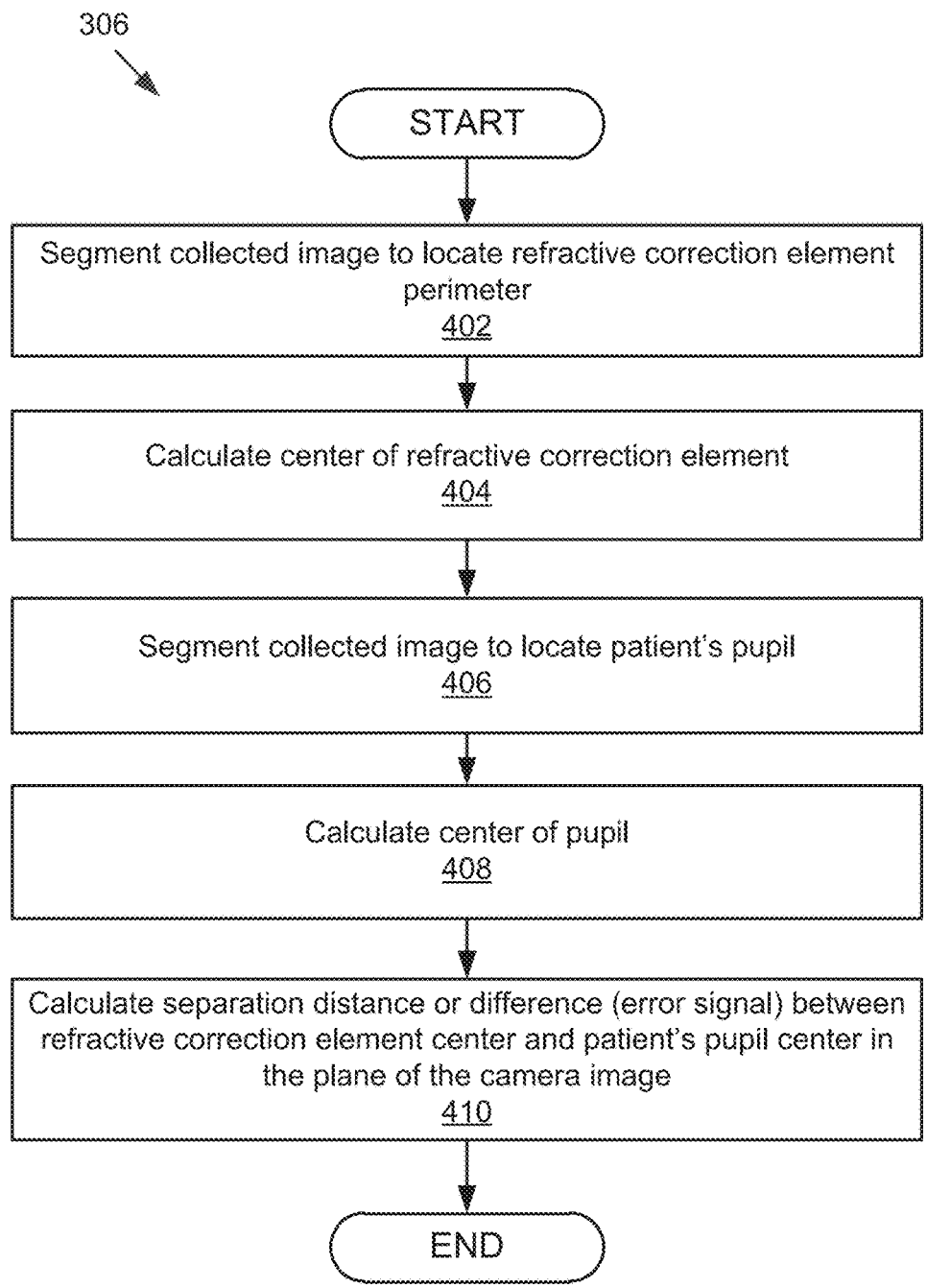
FIG. 4 is a flowchart of an example method for determining relative displacement of a patient's eye with respect to a refractive correction element according to one embodiment of the present invention.

FIG. 4 is a flowchart of a specific method 400 for determining relative displacement of a patient's eye relative to a refractive correction element according to one embodiment of the present invention. Steps 402-410 are performed as part of the instrument control algorithm 605 (see FIG. 6). It should be noted that the functionalities of the instrument control algorithm discussed in the present application are performed in cooperation with a processor (e.g., processor 105) as discussed in further detail below with respect to FIG. 6. It should also be noted that the steps 402-410 are carried out as part of the step 306 in FIG. 3.

In step 402, the instrument control algorithm segments the image collected in step 304 (FIG. 3) to locate the refractive correction element's perimeter and then in step 404, the algorithm calculates the center of the refractive correction element. In step 406, the algorithm segments the collected image to locate the patient's pupil and then in step 408, the center of the pupil is calculated. For instance, the instrument control algorithm receives a live image of the patient's eye from the camera 108 and segments the camera image (e.g., using K-means pixel clustering) to locate the perimeter of the lens aperture and the patient's pupil area. Once the element's perimeter and pupil area are determined, the algorithm then determines the center of each of the refractive correction element and the patient's pupil. Next in step 410, the instrument control algorithm calculates the separation distance in the plane of the camera image between the center of the refractive correction element and the center of the patient's pupil.

In some embodiments, the step 307 of FIG. 3 involves adjusting the position of the patient's eye with respect to the refractive correction element to reduce the separation distance. In one embodiment, this is achieved by the algorithm operating the patient support motors (including chin rest and/or forehead rest motors) of the visual field instrument such that the chin rest and/or the forehead rest moves in the direction that drives the separation distance towards 0. In another embodiment, minimizing the separation distance is achieved by moving the refractive correction element 109 (i.e., actuating the motor connected to the refractive correction element) or the visual field instrument itself in the direction that drives this distance towards a minimal value. In the preferred embodiment, calculation of the separation distance (steps 402-410) and adjustments to reduce the separation distance are done once for each execution of steps 304, 306, and 307 of FIG. 3. However, in some embodiments, once the position(s) of the patient support and/or the refractive correction element are adjusted, steps 402-410 can be re-performed to determine the new difference between the refractive correction element center and the pupil center, and further adjustments can be done if needed based on the new difference. This results in precisely aligning the patient's eye at the center of the refractive correction element.

In some embodiments, the instrument control algorithm may pause perimetry test execution while chin rest, forehead, and/or refractive correction element motor movements are under way if such movements would disrupt test execution. If reduction of the separation distance requires a large movement that would result in an unacceptably long pause, the algorithm may split total movement into segments. One segment will be executed per stimulus presentation. The algorithm will re-assess required movement for each stimulus presentation, regardless of uncompleted segments.

Example Computer System

Figure 6:
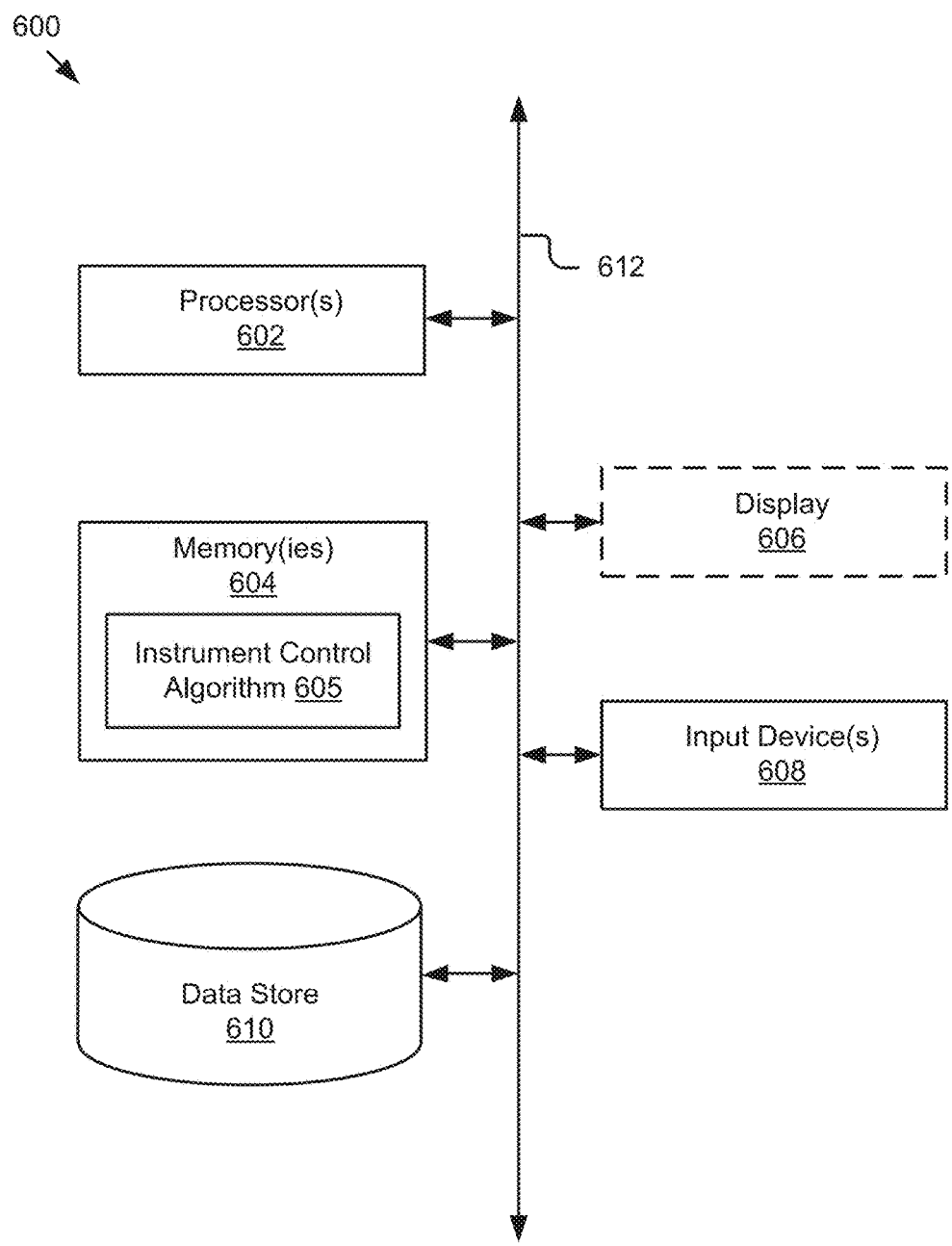
FIG. 6 is a block diagram of a general computer system that may perform the functions discussed in this disclosure according to one aspect of the present invention.

The processing unit or processor 105 that has been discussed herein in reference to FIG. 1 can be implemented with a computer system configured to perform the automatic alignment of a patient's eye with a refractive correction element. For instance, the processing unit 105 can be implemented with the computer system 600, as shown in FIG. 6. The computer system 600 may include one or more processors 602, one or more memories 604, an optional display 606, one or more input devices 608, and a data store 610. The display 606 is shown with dotted lines to indicate it is an optional component, which, in some instances, may not be a part of the computer system 600. In some embodiments, the display 606 discussed herein is the display 110 that has been discussed herein in reference to FIG. 1.

The components 602, 604, 606, 608, and 610 are communicatively coupled via a communication or system bus 612. The bus 612 can include a conventional communication bus for transferring data between components of a computing device or between computing devices. It should be understood that the computing system 600 described herein is not limited to these components and may include various operating systems, sensors, video processing components, input/output ports, user interface devices (e.g., keyboards, pointing devices, displays, microphones, sound reproduction systems, and/or touch screens), additional processors, and other physical configurations.

The processor(s) 602 may execute various hardware and/or software logic, such as software instructions, by performing various input/output, logical, and/or mathematical operations. The processor(s) 602 may have various computing architectures to process data signals including, for example, a complex instruction set computer (CISC) architecture, a reduced instruction set computer (RISC) architecture, and/or architecture implementing a combination of instruction sets. The processor(s) 602 may be physical and/or virtual, and may include a single core or plurality of processing units and/or cores. In some embodiments, the processor(s) 602 may be capable of generating and providing electronic display signals to a display device, such as the display 606, supporting the display of images, capturing and transmitting images, performing complex tasks including various types of feature extraction and sampling, etc. In some embodiments, the processor(s) 602 may be coupled to the memory(ies) 604 via a data/communication bus to access data and instructions therefrom and store data therein. The bus 612 may couple the processor(s) 602 to the other components of the computer system 600, for example, the memory(ies) 604 or the data store 610.

The memory(ies) 604 may store instructions and/or data that may be executed by the processor(s) 602. In the depicted embodiment, the memory(ies) 604 stores at least the instrument control algorithm 605, which may include software, code, logic, or routines, executable by the processor(s) 602, for automatically aligning a patient's eye relative to a refractive correction element as discussed elsewhere herein. For instance, the instrument control algorithm 605 may perform the step 306 (including steps 402-410) and step 307 depicted in FIG. 3. In some embodiments, the memory(ies) 604 may also be capable of storing other instructions and data including, for example, an operating system, hardware drivers, other software applications, databases, etc. The memory(ies) 604 are coupled to the bus 612 for communication with the processor(s) 602 and other components of the computer system 600. The memory(ies) 604 may include a non-transitory computer-usable (e.g., readable, writeable, etc.) medium, which can be any apparatus or device that can contain, store, communicate, propagate or transport instructions, data, computer programs, software, code, routines, etc. for processing by or in connection with the processor(s) 602. A non-transitory computer-usable storage medium may include any and/or all computer-usable storage media. In some embodiments, the memory(ies) 604 may include volatile memory, non-volatile memory, or both. For example, the memory(ies) 604 may include a dynamic random access memory (DRAM) device, a static random access memory (SRAM) device, flash memory, a hard disk drive, a floppy disk drive, a CD ROM device, a DVD ROM device, a DVD RAM device, a DVD RW device, a flash memory device, or any other mass storage device known for storing instructions on a more permanent basis.

The display 606 represents any device equipped to display electronic images and data as described herein. The display 606 may be any of a conventional display device, monitor or screen, such as an organic light-emitting diode (OLED) display, a liquid crystal display (LCD). In some embodiments, the display 606 is a touch-screen display capable of receiving input from one or more fingers of a user. For example, the device 606 may be a capacitive touch-screen display capable of detecting and interpreting multiple points of contact with the display surface.

The input device(s) 608 are any devices for inputting data on the computer system 600. In some embodiments, an input device is a touch-screen display capable of receiving input from one or more fingers of the user. The functionality of the input device(s) 608 and the display 606 may be integrated, and a user of the computer system 600 may interact with the system by contacting a surface of the display 606 using one or more fingers. In other embodiments, an input device is a separate peripheral device or combination of devices. For example, the input device(s) 608 may include a keyboard (e.g., a QWERTY keyboard) and a pointing device (e.g., a mouse or touchpad). The input device(s) 608 may also include a microphone, a web camera, or other similar audio or video capture devices.

The data store 610 can be an information source capable of storing and providing access to data.

In the depicted embodiment, the data store 610 is coupled for communication with the components 602, 604, 606, and 608 of the computer system 600 via the bus 612, and coupled, via the processor(s) 602, for communication with the instrument control algorithm 605. In some embodiments, the instrument control algorithm 605 is configured to manipulate, i.e., store, query, update, and/or delete, data stored in the data store 610 using programmatic operations.

In the above description, for purposes of explanation, numerous specific details are set forth in order to provide a thorough understanding of the specification. It should be apparent, however, that the subject matter of the present application can be practiced without these specific details. It should be understood that the reference in the specification to "one embodiment", "some embodiments", or "an embodiment" means that a particular feature, structure, or characteristic described in connection with the embodiment is included in one or more embodiments of the description. The appearances of the phrase "in one embodiment" or "in some embodiments" in various places in the specification are not necessarily all referring to the same embodiment(s).

The foregoing description of the embodiments of the present subject matter has been presented for the purposes of illustration and description. It is not intended to be exhaustive or to limit the present embodiment of subject matter to the precise form disclosed. Many modifications and variations are possible in light of the above teaching. It is intended that the scope of the present embodiment of subject matter be limited not by this detailed description, but rather by the claims of this application. As will be understood by those familiar with the art, the present subject matter may be embodied in other specific forms without departing from the spirit or essential characteristics thereof. Furthermore, it should be understood that the modules, routines, features, attributes, methodologies and other aspects of the present subject matter can be implemented using hardware, firmware, software, or any combination of the three.

The invention claimed is:

1. A method for performing a visual field test of a patient using a visual field testing device having a refractive correction element, a patient support, and a motor operably attached to one of the refractive correction element or the patient support for changing the location of the refractive correction element relative to the patient support, said method comprising:
positioning the patient's head relative to the visual field testing device using the patient support;
collecting an image of the patient's eye, said image displaying the position of the eye relative to the refractive correction element;
determining the relative displacement of the patient's eye with respect to the refractive correction element based on the collected image, wherein the step of determining the relative displacement includes;
segmenting the image to locate the refractive correction element's perimeter and the patient's pupil;
determining a center of the refractive correction element and a center of the patient's pupil; and
calculating the separation distance between the center of the refractive correction element and the center of the patient's pupil in the plane of the image;
actuating the motor in a manner to reduce the determined displacement;
displaying a series of test stimuli to the eye of the patient;
receiving responses to the test stimuli from the patient;
analyzing the received responses to make an assessment of the patient's visual field; and
displaying or storing the assessment or a further analysis thereof.

2. The method of claim 1, wherein the motor is coupled to the patient support.

3. The method of claim 1, wherein the motor is coupled to the refractive correction element.

4. The method of claim 1, wherein the motor is actuated to eliminate the separation distance.

5. The method of claim 1, wherein the patient support includes one or more of a chin rest and a head rest.

6. The method of claim 1, wherein the refractive correction element is a liquid trial lens.

7. The method of claim 1, wherein the refractive correction element is a conventional or a standard trial lens.

8. The method of claim 1, wherein the collecting, determining, and actuating steps are executed for each testing stimulus displayed to the patient during the course of the visual field test.

9. The method of claim 1, wherein refractive corrective element is a Badal optometer.

10. A visual field testing system for performing a visual field test of a patient, said system comprises:
a patient support for positioning the patient's head relative to the system;
a refractive correction element operably attached to said system for correcting the refractive error of the patient;
a motor operably attached to one of the refractive correction element or the patient support for changing the location of the refractive correction element with respect to the patient support;
a camera for capturing an image of the patient's eye, said image displaying the position of the patient's eye relative to the refractive correction element;
a processor for determining the relative displacement of the patient's eye with respect to the refractive correction element based on the captured image
and wherein the relative displacement is determined by segmenting the image to locate the refractive correction element's perimeter and the patient's pupil, determining a center of the refractive correction element and a center of the patient's pupil, and calculating the separation distance between the center of the refractive correction element and the center of the patient's pupil in the plane of the image, said processor for actuating the motor in a manner to reduce the determined displacement;
a display for displaying a series of test stimuli to the eye of the patient; and
a response mechanism for receiving patient responses to the test stimuli.

11. The visual field system of claim 10, wherein the motor is coupled to the patient support.

12. The visual field system of claim 10, wherein the motor is coupled to the refractive correction element.

13. The visual field system of claim 10, wherein the motor is actuated to eliminate the separation distance.

14. The visual field system of claim 10, wherein the patient support includes one or more of a chin rest and a head rest.

15. The visual field system of claim 10, wherein the refractive correction element is a liquid trial lens.

16. The visual field system of claim 10, wherein the refractive correction element is a conventional or a standard trial lens.

17. The visual field system of claim 10, wherein the refractive correction element is a Badal optometer for the refractive error correction of the patient.

* * * * *